United States Patent [19]

Razauskas et al.

[11] Patent Number: 5,024,081
[45] Date of Patent: Jun. 18, 1991

[54] LOCATING FLAT SPOTS ON RUBBER WIPE ROLLS

[75] Inventors: Anthony F. Razauskas, Pasadena; Marlie A. Duncan, Upperco, both of Md.

[73] Assignee: The Ward Machinery Company, Cockeysville, Md.

[21] Appl. No.: 570,016

[22] Filed: Aug. 20, 1990

[51] Int. Cl.⁵ ............................................. G01N 19/08
[52] U.S. Cl. ..................................................... 73/104
[58] Field of Search .................................. 73/104, 105

[56] References Cited

U.S. PATENT DOCUMENTS

| | | | |
|---|---|---|---|
| 2,240,278 | 4/1941 | Abbott | 73/105 |
| 3,194,061 | 7/1965 | Sorenson et al. | 73/104 |
| 4,858,465 | 8/1989 | Molina | 73/104 |

Primary Examiner—Robert Raevis
Attorney, Agent, or Firm—Boyce C. Dent; Edward D. C. Bartlett

[57] ABSTRACT

A method of testing a resiliently covered roll for surface flat spots involves rotating the roll and applying a film of water with a sponge roller to at least a portion of the length of the rotating roll surface. Then doctoring the rotating surface with a blade to remove the film, and detecting any flat spot by observing any puddle of water remaining after the doctoring. A testing device preferably is handheld and comprises a forwardly extending doctor blade below which is rotatably mounted the sponge roller. A rubber wipe roll for flexographic printing can be so advantageously tested for flat spots before installation.

16 Claims, 4 Drawing Sheets

LOCATING FLAT SPOTS ON RUBBER WIPE ROLLS

FIELD OF THE INVENTION

This invention relates to locating flat spots on rolls, particularly resiliently covered rolls such as rubber wipe rolls used in printing. The invention relates to both a method of determining whether such rolls have flat spots and a device for use in performing the method.

BACKGROUND OF THE INVENTION

Rolls having their cylindrical surface formed by a resilient material cover, for example a rubber covered wipe roll as used in flexographic printing, at times develop flat spots, or areas, on the surface. It is believed this occurs when the surface is distorted, or flattened, for too long a period of time, e.g. during transportation. It has been customary to dial the surface of these rolls with a dial instrument to test for concentricity before use. However, such dialling does not necessarily detect any flat spots in the cylindrical surface. Such flat spots are usually only detected after the roll is assembled in a printing machine and printing commenced; any flat spot then becomes apparent, as it creates an area of over inking of the material being printed, e.g. corrugated container blanks. The defective roll then has to be removed from the printing machine and replaced. It may be possible to salvage the defective roll after removal by re-grinding a new surface.

SUMMARY OF THE INVENTION

It is an object of the invention to provide a method of testing rolls, particularly rubber wipe rolls, for flat spots before installation into the machinery in which the rolls are to be used.

A feature by which this is achieved is by applying a film of liquid to the roll to be tested, and then removing this film with a doctor blade. Any flat spot will show up as a puddle of liquid remaining on the roll surface after doctoring.

According to one aspect of the invention there is provided a method of testing a roll for surface flat spots comprising rotating the roll and applying a liquid film with a sponge roller to at least a portion of the length of the rotating roll surface. Then doctoring the rotating surface with a blade to remove the film, and detecting any flat spot by observing any puddle of liquid remaining after the doctoring.

The liquid film can be applied using any form of liquid which, preferably, may be colored, e.g. by a coloring agent or dyestuff. The term liquid is used herein to include liquid in the form of a gel. A wetting agent may be added to the liquid.

A flat spot testing device according to the invention is preferably handheld and comprises a forwardly extending doctor blade below which is rotatably mounted the sponge roller.

Using the above method and testing device, a rubber wipe roll for flexographic printing can be advantageously tested for flat spots before installation.

According to a preferred aspect of the present invention, there is provided a method of testing a cylindrical surfaced, rubber covered wipe roll for surface flat spots comprising the steps of mounting the wipe roll in a test stand for free rotation therein, rotating the wipe roll by hand in the test stand, and holding a test device against the cylindrical surface of the wipe roll to apply a film of water to a portion of the cylindrical surface with a sponge roller of the test device and then immediately remove this water film with a doctor blade of the test device. This holding step is repeated by moving the test device to successive adjacent axial locations along the wipe roll. Any flat spot on the wipe roll is detected by observing any puddle of water remaining after the water film is removed by the doctor blade.

According to another aspect of the invention, there is provided a device for testing a cylindrical surfaced roll for flat spots, comprising upper and lower body parts releasably secured together, a doctor blade clamped between the body parts and extending therefrom in a forward direction, and a handle arrangement connected to at least one of the body parts and extending therefrom in a rearward direction opposite to the forward direction. A pair of brackets extend downwardly from the lower body part with a sponge roller supported by and rotatable between the brackets. The sponge roller is mounted on an axle which is carried by the brackets, the axle being parallel to the blade.

Other objects, features and advantages of the present invention will become more fully apparent from the following detailed description of the preferred embodiment, the appended claims and the accompanying drawings.

BRIEF DESCRIPTION OF THE DRAWINGS

In the accompanying drawings, in which like reference characters in the same or different Figures indicate like parts.

DETAILED DESCRIPTION OF THE PREFERRED EMBODIMENT

Figure 1:
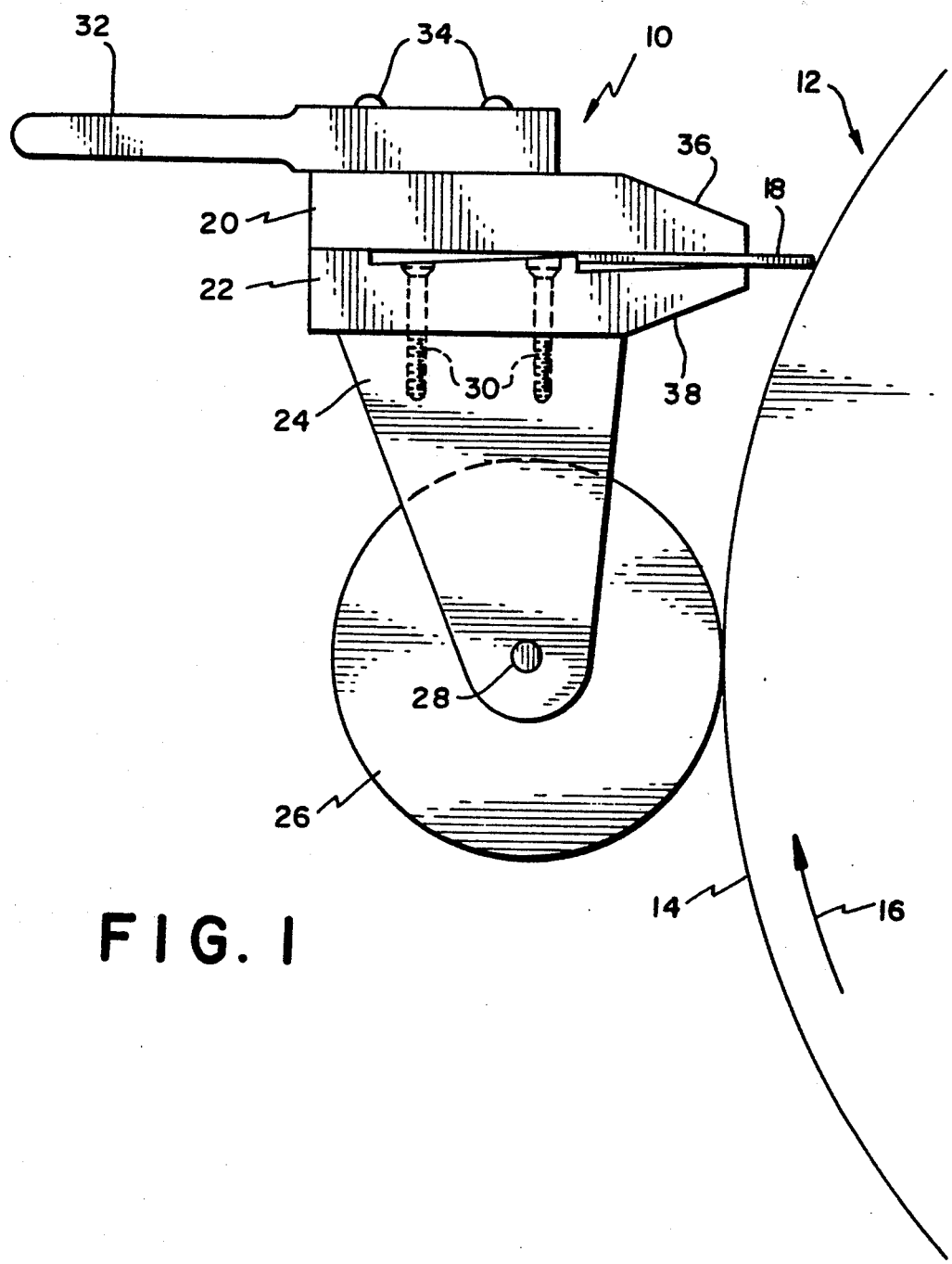
FIG. 1 is a diagrammatic side view of a flat spot detecting device according to the invention and shown in use on a resiliently covered roll.
Figure 3:
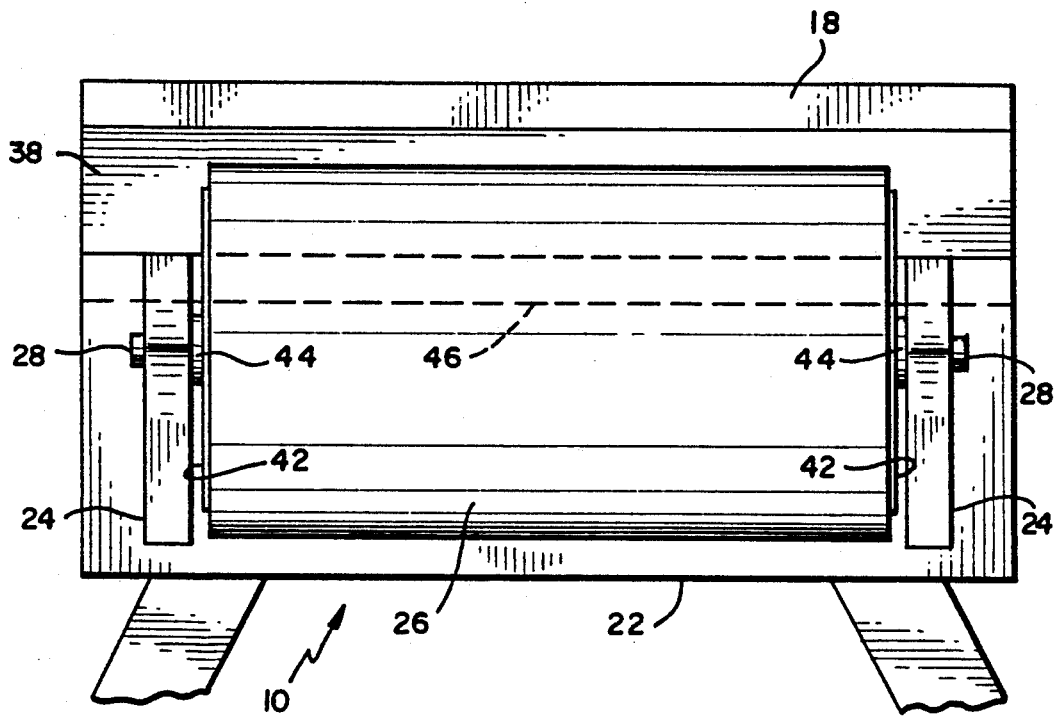
FIG. 3 is a bottom plan view of the device of FIG. 2 with portions of the handles omitted for simplicity.
Figure 4:
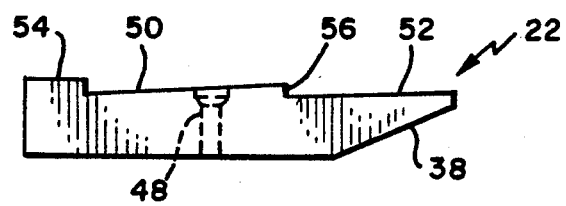
FIG. 4 is an end side view in the direction of the arrow 4 in FIG. 2 of an underneath blade clamping member of the device of FIGS. 1, 2 and 3.
Figure 5:
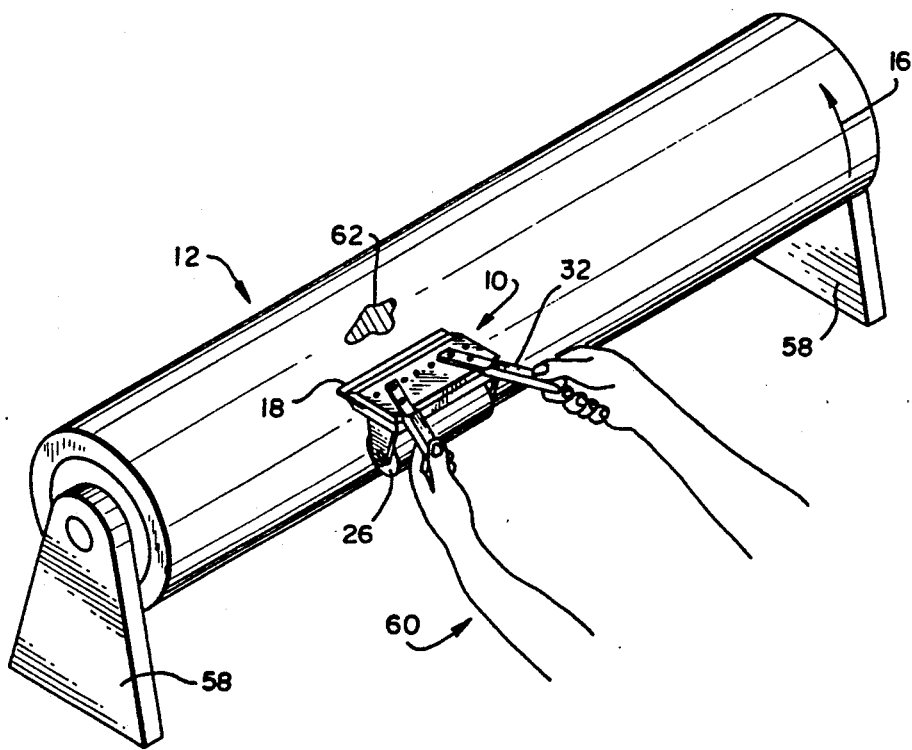
FIG. 5 is a perspective illustration of the roll in FIG. 1 being tested with the flat spot detecting device of FIGS. 1 to 4 and locating a flat spot.

The preferred embodiment of the flat spot detecting device is shown in FIGS. 1 to 5 with FIGS. 1 and 5 showing the device 10 in use testing a rubber wipe roll 12.

FIG. 1 shows a side view of the device 10 applied in use against the cylindrical rubber covered surface 14 of the wipe roll 12, the latter being rotated upwardly in the direction of the arrow 16. The device 10 has a thin straight edge blade 18 clamped between upper and lower clamp body parts 20, 22. The lower body part 22 has a pair of downwardly extending end brackets 24 (see also FIG. 3) between which an open cell sponge roller 26 is rotatably mounted, a central axle shaft 28 on which the roller 26 rotates being secured through the lower ends of the brackets 24. Each bracket 24 is rigidly secured to the lower body part 22 by a pair of countersunk screws 30 as indicated in FIG. 1. A pair of rearwardly extending and outwardly diverging handles 32 (see also FIGS. 2, 3 and 5) are each secured to the upper surface of the upper body part 20 by two screws 34. The front of the clamping body parts 20, 22 are forwardly tapered inwardly towards the extending portion of the blade 18 as clearly shown at 36, 38 in FIG. 1. The lower body part 22 has an upper stepped surface as will be described in relation to FIG. 4 later; the blade 18 only extends rearwardly halfway between the clamping body parts 20, 22.

Figure 2:
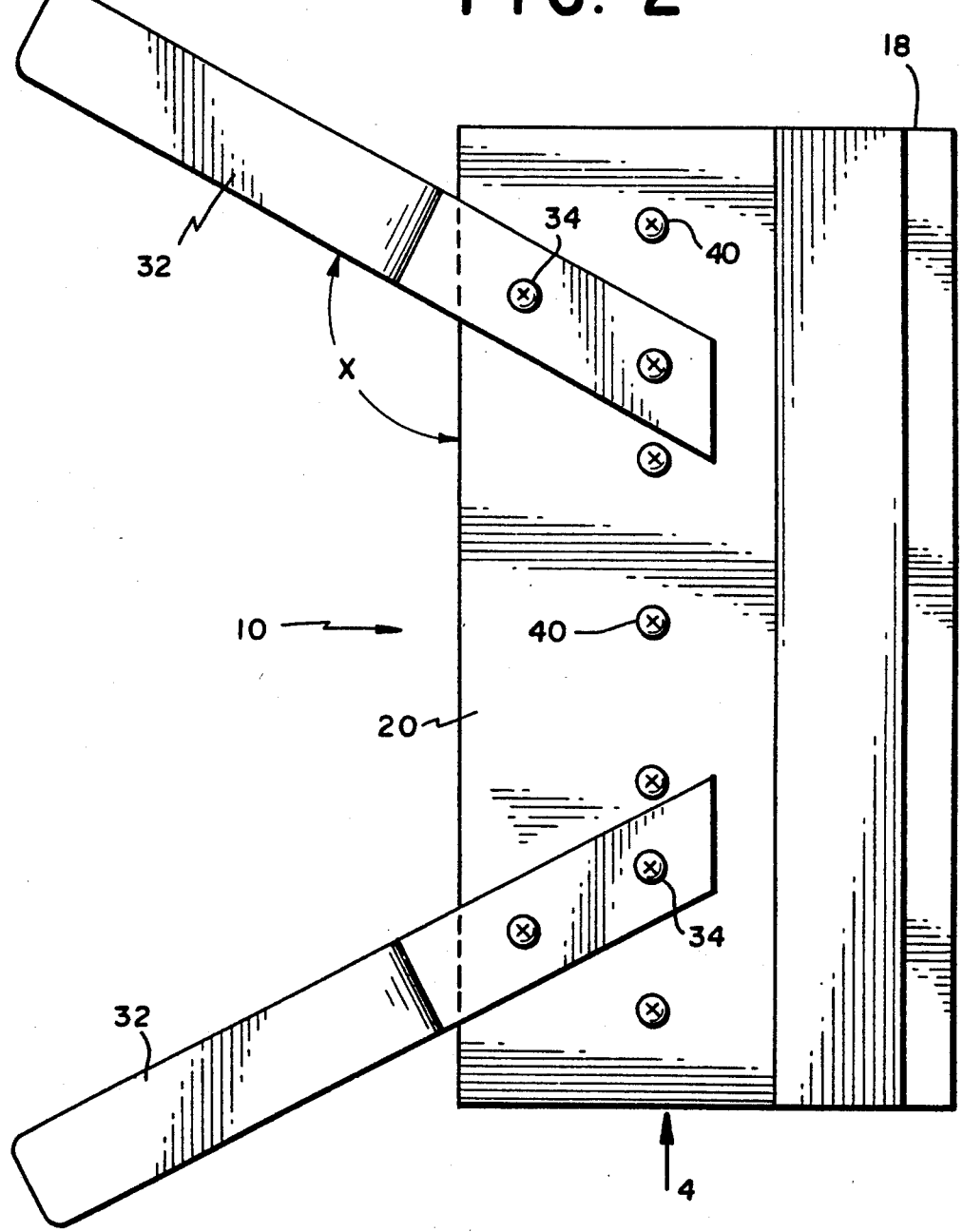
FIG. 2 is a top plan view of the flat spot detecting device of FIG. 1.

FIG. 2 shows in top view the two handles 32 each making an obtuse angle x with the rear edge of the device 10 so that the handles 32 rearwardly diverge from each other at an angle of 2x minus 180 degrees. It has been found convenient to have the angle x to be about 115 degrees so that the handles are at an angle of about 50 degrees to each other. Five screws 40 removably clamp the upper body part 20 to the lower body part. The blade 18 extends forwardly of the clamped body parts across the full width of the device 10.

FIG. 3 is an underneath view of the device 10 and shows the brackets 24 inset from the ends of the lower body part 22 with the absorbent sponge roller mounted therebetween. The roller 26 thus extends across the device 10 for less than the width thereof. The roller 26 has plastic end flange discs 42 with central bosses 44 freely rotatable on the axle 28. The sponge roller 26 is held between the discs 42 and rotates on the axle with these discs 42. The roller 26 is constructed and rotatably mounted similarly to a paint applicator roller. The rearward edge of the portion of the blade 18 clamped between the body parts 20, 22 is indicated by the broken line 46.

FIG. 4 is a side view of one end of the lower body part 22 (as also seen in FIG. 1). Each of the screws 40 (FIG. 2) is screwed into a vertical threaded bore 48 in the lower body part 22. The upper surface of the body part 22 is formed with a rear step 50 and a front step 52. The rear step 50 terminates rearwardly with a shoulder 54 along the upper rear edge of the body part 22. The steps 50, 52 are each inclined upwardly and forwardly at a small acute angle of about 2 degrees to the horizontal, i.e. to the general clamping plane between the upper and lower body parts. The blade 18 is clamped by the step 52 against the upper body part with the rear edge 46 of the blade 18 (see FIG. 3) abutting the vertical stop surface 56 between the steps 50, 52. The small upwards and forward inclination of the upper surfaces of the steps 50, 52 improves the clamping grip on the blade 18.

FIG. 5 illustrates the rubber covered wipe roll 12 being tested for flat spots by the testing device 10. The wipe roll 12 is mounted in and between two roll stand frame members 58. The wipe roll 12 is freely rotatable when so supported, and can readily be rotated by one hand of an operator 60.

To test the wipe roll 12 for flat spots, the operator dips the sponge roller 26 in a container of water to load the sponge 26 with water. Then, by hand, the operator commences the wipe roll 12 rotating fairly slowly in an upward direction with respect to the operator as shown by the arrow 16. The operator 60 then stands as illustrated grasping a handle 32 in each hand and lightly pressing the sponge roller 26 and the free extending edge of the blade 18 against the surface of the rotating wipe roll 12. The blade 18 is held in an approximately horizontal plane with the sponge roller 26 below the blade 18. The sponge roller is located at approximately midway up the wipe roll 12 (i.e. on approximately a horizontal diametrical plane of the wipe roll) so that the blade contacts an upper portion of the wipe roll. In this way, as can be seen in FIG. 1, the blade 18 makes an acute angle with the approaching surface of the wipe roll, this angle preferably being in the range 40 to 70 degrees, for example 60 degrees. As the wipe roll surface moves upwards, the sponge roller 26 applies a film of water thereto as the sponge roller is rotated by contact with the wipe roll surface. This film is applied as a band the width of the sponge roller 26. Immediately thereafter, the blade 18 functions as a doctor blade to doctor and remove this water film. However, if there is a flat spot (or depressed area) in the surface of the wipe roll, then water will be left covering that flat spot as the flat spot will not contact the blade 18. It has been found that any such puddle of water in or on a flat spot shows up clearly on the wipe roll surface and can readily be seen in normal lighting conditions. A water puddle 62 is shown on wipe roll 12 indicating a flat spot at that location in the roll surface. The complete surface of the wipe roll can be tested by starting at one end and progressively rolling overlapping bands of water film completely around the cylindrical surface of the wipe roll. The sponge roller 26 should periodically be re-loaded with water; also, the wipe roll 12 may from time to time require additional hand movement from the operator to keep it slowly rotating during the test. It would also be possible to motorize slow rotation of the roll being tested.

Preferably, a wetting agent is added to the water before the sponge roller is loaded. This advantageously enables the water film to be more uniformly applied; this also more clearly defines any puddle left after wiping and indicating a flat spot.

If a flat spot(s) is detected, then the roll is rejected. Depending upon the construction and intended purpose of the defective roll, it could be rectified by re-grinding its surface or by recovering it.

The dimensions of the device 10 were width 11.75 inches, overall depth front to back 3.25 inches of which the blade protruded 0.75 inch, thickness of blade 0.0625 inch, and diameter of sponge roller 1.75 inches. The handles 32 were 8 inches in overall length. A typical rubber covered wipe roll 12 has a diameter of 10 inches and may be 80 to 123 inches in axial length.

The doctor blade 18 is preferably made from sheet mylar. It could also conveniently be made from polyethylene or steel. It is important that the blade has and maintains a straight edge in contact with the roll being tested.

Apart from pre-testing a roll for flat spots before the roll is mounted in machinery for use, the testing device 10 could also be used in the above manner to test a roll in situ for any suspected flat spot.

The water, or any other liquid (including any gel) used, can advantageously be colored by a suitable dye or coloring agent, e.g. may be colored orange, red, blue, or black. This is particularly useful when the roll being tested has a white or light colored surface as it enables any residual puddle to be observed more readily.

The above described embodiments, of course, are not to be construed as limiting the breadth of the present invention. Modifications, and other alternative constructions, will be apparent which are within the spirit and scope of the invention as defined in the appended claims.

What is claimed is:

1. A method of testing a cylindrical surfaced roll for flat spots, comprising the sequential steps of:

applying a liquid film to the cylindrical surface of the roll;

wiping the liquid film off the roll with a blade; and detecting any flat spot on the cylindrical surface of the roll by observing the presence of any puddle of liquid left on the cylindrical surface after said wiping.

2. The method of claim 1, wherein said liquid film is applied by a sponge roller.

3. The method of claim 1, wherein said liquid film is colored to enable any said puddle to be observed more readily.

4. The method of claim 1, wherein the liquid film is applied as a gel.

5. The method of claim 1, wherein the roll is a resiliently covered wipe roll for printing apparatus.

6. The method of claim 1, wherein the roll is a rubber covered wipe roll.

7. The method of claim 1, wherein successive bands of liquid film are applied to the cylindrical surface, each band being wiped off before the next band is applied.

8. The method of claim 1, comprising an initial step of mounting the roll for free rotation in a test roll stand, and effecting said applying step by rotating said roll by hand and holding a liquid loaded sponge roller against the rotating roll.

9. The method of claim 8, wherein said doctor blade is positioned adjacent said sponge roll downstream thereof with respect to the direction of rotating of said roll.

10. A method of testing a resilient covered roll for surface flat spots, comprising:

rotating the roll;

applying a film of liquid with a liquid loaded sponge roller to a portion of the surface of the roll while rotating;

using a blade to remove said film from the surface of the rotating roll; and detecting any flat spot on said portion of the surface by observing any puddle of liquid remaining after said using of the blade to remove said film.

11. The method of claim 10, wherein said roll has an axial length and bands of liquid are successively applied to adjacent axial portions along the axial length of the roll.

12. The method of claim 11, wherein each said band is removed by said blade using step before the next successive band is applied.

13. The method of claim 12, wherein said liquid comprises colored water.

14. The method of claim 10, wherein said liquid comprises water.

15. A method of testing a cylindrical surfaced, rubber covered wipe roll for surface flat spots, comprising the steps of:

mounting the wipe roll in a test stand for free rotation therein;

rotating the wipe roll in the test stand;

holding a test device against the cylindrical surface of the wipe roll to apply a film to a portion of the cylindrical surface with a sponge roller of the test device and then immediately remove this film with a blade of the test device;

repeating the holding step by moving the test device to successive adjacent axial locations along the wipe roll; and detecting any flat spot on the wipe roll by observing any puddle remaining after the film is removed by the doctor blade.

16. The method of claim 15, wherein the film comprises water, the test device is handheld, the sponge roller is rotated by contact with the wipe roll, the wipe roll is rotated by hand, and further comprising the step of periodically dipping the sponge roller in a container of water to periodically load the sponge roller with water.

* * * * *